United States Patent
Tange

(10) Patent No.: US 7,298,470 B2
(45) Date of Patent: Nov. 20, 2007

(54) DEFECT INSPECTION DEVICE FOR METAL RING END FACES OF A CONTINUOUSLY VARIABLE TRANSMISSION BELT

(75) Inventor: Hiroshi Tange, Fuji (JP)

(73) Assignee: JATCO Ltd (JP)

( * ) Notice: Subject to any disclaimer, the term of this patent is extended or adjusted under 35 U.S.C. 154(b) by 246 days.

(21) Appl. No.: 11/090,014

(22) Filed: Mar. 28, 2005

(65) Prior Publication Data

US 2005/0219538 A1   Oct. 6, 2005

(30) Foreign Application Priority Data

Mar. 29, 2004   (JP) ............... 2004-097236

(51) Int. Cl.
*G01N 21/00* (2006.01)
(52) U.S. Cl. .................. 356/237.2; 256/237.1
(58) Field of Classification Search .......... 250/559.42, 250/55.9, 55, 9.45–9.6; 356/237.1, 430; 474/201, 242; 702/33–36, 40, 167, 172
See application file for complete search history.

(56) References Cited

U.S. PATENT DOCUMENTS

| 4,715,709 | A  | * | 12/1987 | Sekine et al. ............ 356/237.2 |
|---|---|---|---|---|
| 5,164,603 | A  | * | 11/1992 | Hartman et al. ........ 250/559.46 |
| 5,640,868 | A  | * | 6/1997  | Lauener ..................... 72/110 |
| 6,166,393 | A  | * | 12/2000 | Paul et al. ............. 250/559.08 |
| 6,613,334 | B2 | * | 9/2003  | Yoshida et al. ............ 474/242 |
| 6,684,473 | B1 | * | 2/2004  | Yamagishi et al. ...... 29/407.01 |
| 6,779,414 | B2 | * | 8/2004  | Shori et al. ................ 73/865.9 |
| 6,989,548 | B2 | * | 1/2006  | Tange et al. ........... 250/559.45 |
| 7,113,872 | B2 | * | 9/2006  | Tange et al. ................... 702/35 |

FOREIGN PATENT DOCUMENTS

| JP | 8-147467    | 6/1996  |
|----|-------------|---------|
| JP | 09-304288   | 11/1997 |
| JP | 11-117017   | 4/1999  |
| JP | 11-200010   | 7/1999  |
| JP | 11-248637   | 9/1999  |
| JP | 2003-139523 | 5/2003  |
| JP | 2004-077425 | 3/2004  |

OTHER PUBLICATIONS

Netherlands Search Report, Dec. 12, 2005.

* cited by examiner

*Primary Examiner*—Layla G. Lauchman
*Assistant Examiner*—Jarreas Underwood
(74) *Attorney, Agent, or Firm*—Blank Rome LLP

(57) ABSTRACT

A defect inspection device for metal ring end faces of a Continuously Variable Transmission (CVT) V-belt which enables automated inspection of end face defects in the metal rings along with acquiring improved efficiency, superb precision and reproducibility. When end face defects in the metal ring are inspected by an inspection section, this task is accomplished by an angle modification portion which performs an angle modification operation continuously in a predetermined range ($\theta_1 \sim \theta_5$) relative to an inspectable surface for at least a first light guiding path and a second light guiding path included in the defect inspection section. Because this automated modification operation corresponds to processing by manual visual inspection and applies a common practice detection method used in labor-intensive visual inspections by changing the viewing angle to detect defects, such as a gloss mark, the object of the present invention can be achieved.

3 Claims, 12 Drawing Sheets

No alarm signal ALM generated

Alarm signal ALM generated

DEFECT INSPECTION DEVICE FOR METAL RING END FACES OF A CONTINUOUSLY VARIABLE TRANSMISSION BELT

BACKGROUND OF THE INVENTION

1. Field of the Invention

The present invention relates to a defect inspection device for metal rings. More particularly, the present invention relates to a defect inspection device suitable for inspecting the presence of end face defects on metal rings which are parts that constitute a V-belt type of a Continuously Variable Transmission belt (hereinafter denoted as "CVT belt") mounted in a vehicle, such as an automobile.

2. Description of the Related Art

As a CVT belt, for example, there is a known CVT belt structure which laminates a plurality of thin metal rings in a stack of approximately 0.2 mm in thickness to which steel elements are consecutively attached.

FIG. 10 is an outline view of a CVT belt. In this diagram, a CVT belt 1 is constructed by assembling two laminated bands of a layered belt 3 that contain a stack of a number of metal rings 2 (for example, a laminated band composed of about 12 endless layers) which are supported by a layered element 5 composed of a large number of steel elements 4 (for example, about 400 elements).

FIG. 11 is an outline diagram of the manufacturing process of the CVT belt 1. Referring to this drawing, the end parts 6a of an "ultrahigh strength steel" thin sheet 6 (described later in detail) are welded together and a drum 7 is formed. Next, the drum 7 is cut into round slices of predetermined width and rolled to create metal rings 2 of a basic peripheral length.

Next, after performing a solution treatment, etc. to each of the above-mentioned metal rings 2, a peripheral length correction process is performed that provides the necessary peripheral length corresponding to the lamination location on the CVT belt 1. Here, "peripheral length" means the circumference length of the metal rings 2. The peripheral lengths of the metal rings 2 are subtly different for each lamination stacked position in the CVT belt 1. For example, the outermost periphery side is slightly longer and the innermost periphery side is slightly shorter.

After the peripheral length correction process and further performing aging treatment, nitride treatment, etc. to increase the hardness of the metal rings 2, the presence of surface defects in the metal rings 2 is inspected. The metal rings 2 which pass a quality control inspection are sequentially laminated together in a stack of about 12 layers to form a laminated band which becomes a CVT belt. The steel elements 4 are inserted are consecutively attached and the CVT belt 1 is completed.

As stated above, ultrahigh strength steel is used for the metal rings 2 of the CVT belt 1. As a type of ultrahigh steel suitable for a CVT belt 1 there is maraging steel, for example, as described in Japanese Laid-Open Patent Application No. H11-117017 (1999) titled "CARBURIZATION SURFACE HARDENING OF MARAGING STEEL". Although maraging steel is ideal for use in the CVT belt 1 because of its characteristic dynamic fracture toughness, it is not sufficient in regard to its structural impact-fatigue strength properties. In order to compensate this fatigue strength, nitriding treatment is performed, for example, as described in Japanese Laid-Open Patent Application No. H11-200010 (1999) titled "SURFACE TREATMENT OF METALLIC MULTILAYERED BELT FOR AUTOMOBILE".

Nitriding treatment is a process in which nitrogen permeates the front surface of the steel and forms a hardening layer (hardened membrane). Although a salt bath nitriding process, a tuffride salt bath nitriding process, a plasma nitriding process, a gas nitrocarburizing process, etc. are known, generally in mass production components such as the CVT belt 1, gas nitrocarburizing is used in terms of cost. Based on this method, a surface hardening layer of about HV 400~700 (HV=the Vickers hardness number, an indicator of the hardness of metal) is formed on the steel surface to a depth of about 8~15 μm (micrometers).

Furthermore, as the hardening layer is formed on the front face of the metal rings 2 and because the metal rings 2 are extremely thin (at most about 0.2 mm), a flaw (herein after denoted as an "end face defect") may often be scarred on the side end faces in the manufacturing process of the CVT belt 1.

FIG. 12 is a diagram showing an end face defect in one of the metal rings 2. For the moment, suppose that an end face defect exists in the "a" section of FIG. 12A. FIG. 12B is a microscopic enlargement diagram (magnification: around 480 times) of this "a" section and FIG. 12C is a similar pattern diagram. As shown in FIG. 12C, a defect 2b scar by some cause is observed in the end face 2a of the metals rings 2. The defect 2b is a defective portion in the hardened layer which is clearly glossy and visible as a shiny white portion (gloss mark) as compared with the non-defective portion (hatching portion).

Conventionally, the inspection for such end face defects is performed by direct visual observation with the aid of a magnifying glass. In short, the end face 2a of the metal rings 2 is held up to the light one by one by a factory worker to artificially judge the subtle differences in gloss. However, such a manual inspection method as described above is antiquated and inefficient due to the fact that human error rate is always higher than an automated process. The accepted level of variation depends greatly on each factory worker. Thus, there is a drawback in acquiring a consistent level of inspection accuracy to further improve reproduction.

Therefore, the object of the present invention is to provide a defect inspection device for metal ring end faces which enables automated inspection of end face defects in metal rings 2 along with acquiring improved inspection efficiency, superb precision and reproducibility.

SUMMARY OF THE INVENTION

A defect inspection device for metal ring end faces of a Continuously Variable Transmission (CVT) V-belt comprises at least two belt pulleys; a rotary driving means for rotating the pulleys and a metal ring as an object to be inspected wound around the belt pulleys and for providing circumferential movement to the metal ring; a tension assignment means for providing a predetermined tension to the metal ring while regulating the spacing of the belt pulleys during rotation; a defect inspection section for inspecting a side end face defect on an inspectable surface of the metal ring during circumferential movement. The defect inspection section includes a light source for illuminating the inspectable surface of an object to be inspected; a first light guiding path for guiding a reflected light from the inspectable surface to a first light detector and a second light guiding path for guiding the reflected light to a second light detector; a difference value calculation means for calculating a difference value between an electrical signal outputted from the first light detector or an electrical signal correlated to its electrical signal and an electrical signal outputted from the second light detector or an electrical signal correlated to its electrical signal; a discrimination means for discriminating the presence of a defect on the inspectable surface and comparing the difference value with a predetermined threshold value; and further comprises an angle modification means for performing an angle modification operation continuously in a predetermined range relative to the inspectable surface of the first light guiding path and the second light guiding path.

According to the present invention, the angle modification means performs an angle modification operation continuously in a predetermined range relative to the inspectable surface of the first light guiding path and the second light guiding path along a predetermined circular arc; and the predetermined circular arc forms a portion of a circle which centrally traces an arc above the spacing close to the inspectable surface.

According to the present invention, the angle modification means includes a plate; a guide groove circular arc formed in the plate; a mounting board for performing reciprocation along the guide groove; the first light guiding path and the second light guiding path at least are mounted on the mounting board; and the guide groove circular arc forms a portion of a circle which centrally traces an arc based on a supporting point above the spacing close to the inspectable surface.

Here, "the angle relative to the inspectable surface of the first light guiding path and the second light guiding path" indicates the angle of the optical axis centerline of the first light guiding path and the second light guiding path as well as the inspectable surface.

Based on the present invention, when end face defects in the metal rings are inspected by the inspection section, this task is accomplished by an angle modification means which performs an angle modification operation continuously in a predetermined range relative to an inspectable surface for at least a first light guiding path and a second light guiding path included in the defect inspection section.

Because this automated modification operation corresponds to processing by manual visual inspection (processing by variously changing the visual recognition direction relative to the end face 2a of the metal rings 2) and applies a common practice detection method used in labor-intensive visual inspections by changing the viewing angle to detect defects, such as a gloss mark (When performing a visual inspection by changing the angle of the metal rings 2, a gloss mark on an end face 2a is easy to detect.), the object of the present invention can be achieved.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

DETAILED DESCRIPTION OF THE PREFERRED EMBODIMENTS

The preferred embodiments of the present invention will hereinafter be described in detail with reference to the drawings. Additionally, in the following explanation of specific or examples of various details, numerical values or character strings and other illustrative symbols are merely references to clarify the concept of the present invention. Accordingly, the concept of the present invention should not be limited explicitly to this terminology entirely or in part.

In addition, explanation is omitted which describes details of well-known methods, well-known procedures, well-known architecture, well-known circuit configurations, etc. (hereinafter denoted as "common knowledge") for the purpose of concise explanation, but does not intentionally exclude this common knowledge entirely or in part. Therefore, relevant common knowledge already known by persons skilled in the art at the time of filing the present invention is naturally included in the following description.

Figure 1:
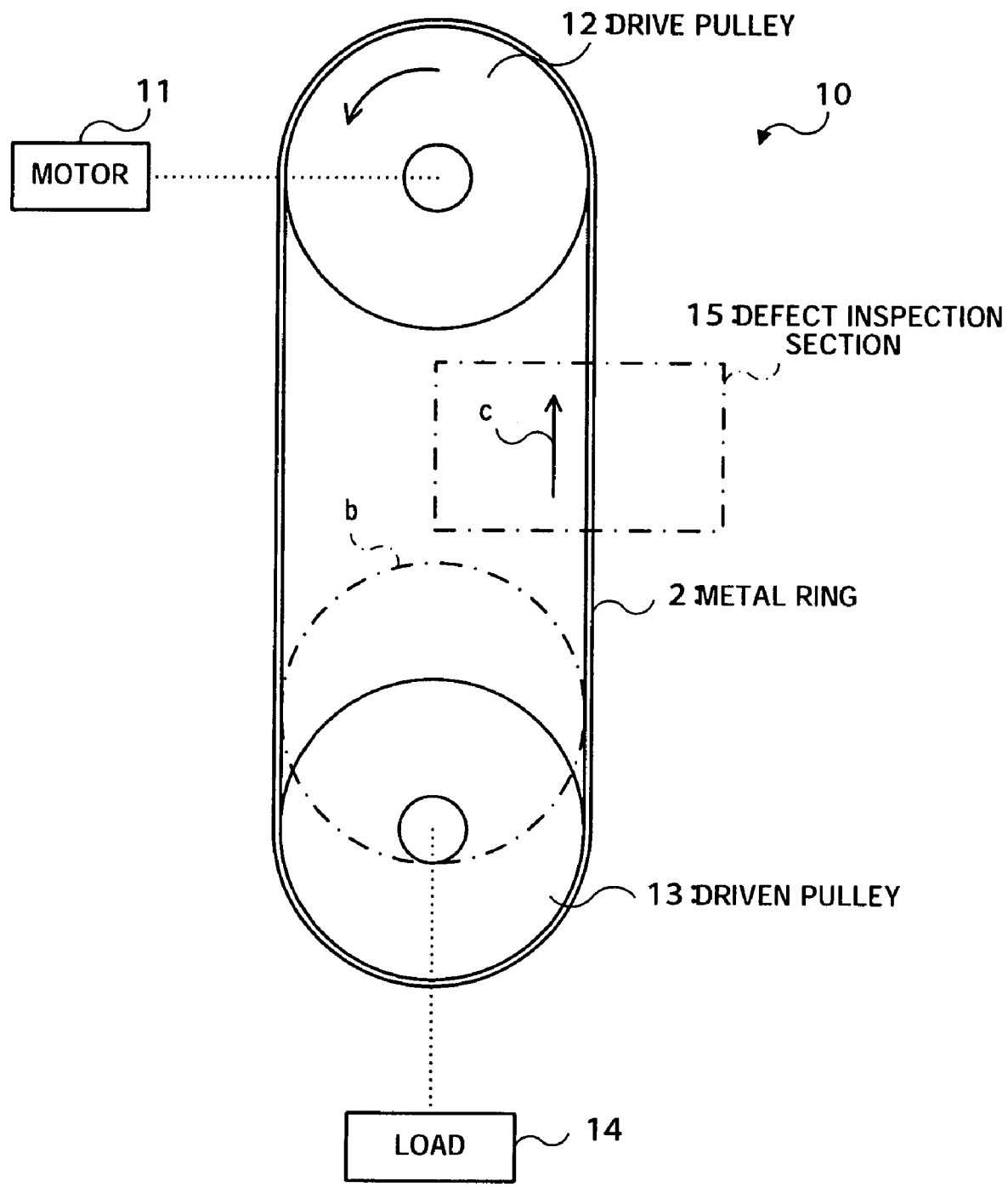
FIG. 1 is a conceptual line block diagram of a defect inspection device for metal ring end faces.

FIG. 1 is a conceptual line block diagram of a defect inspection device for metal ring end faces. A defect inspection device 10 for metal ring end faces comprises a fixed position drive pulley 12 which is rotary driven by a motor 11 (rotary driving means) for metal ring circumferential drive, a variable position driven pulley 13 which is separately situated on the same rotational plane as the drive pulley 12, a load 14 (tension assignment means) which has a predetermined mass (for example, 80 kg) and a defect inspection section 15. Besides the drive pulley 12 and the driven pulley 13 there can be one or a plurality of additional guide pulleys, but the requisite minimum number of pulleys is two: the drive pulley 12 and the driven pulley 13. The description of "at least two pulleys" in the above summary of the invention indicates this requisite minimum number of belt pulleys.

When inspecting the metal rings 2 which are objects to be inspected, first, the driven pulley 13 is positioned at an initial position (refer to position "b" on the dashed dotted line). Subsequently, the metal rings 2 are wound around the two pulleys (drive pulley 12 and driven pulley 13). Next, the desired tension is applied to the metal rings 2 by furnishing a load 14 which drives the driven pulley 13. Then, in the state of operating the motor 11 for ring circumferential drive which causes the metal rings 2 to rotate unidirectionally (the direction of arrow "c"), an end face inspection of the applicable metal rings 2 is performed using the defect inspection section 15.

Figure 2:
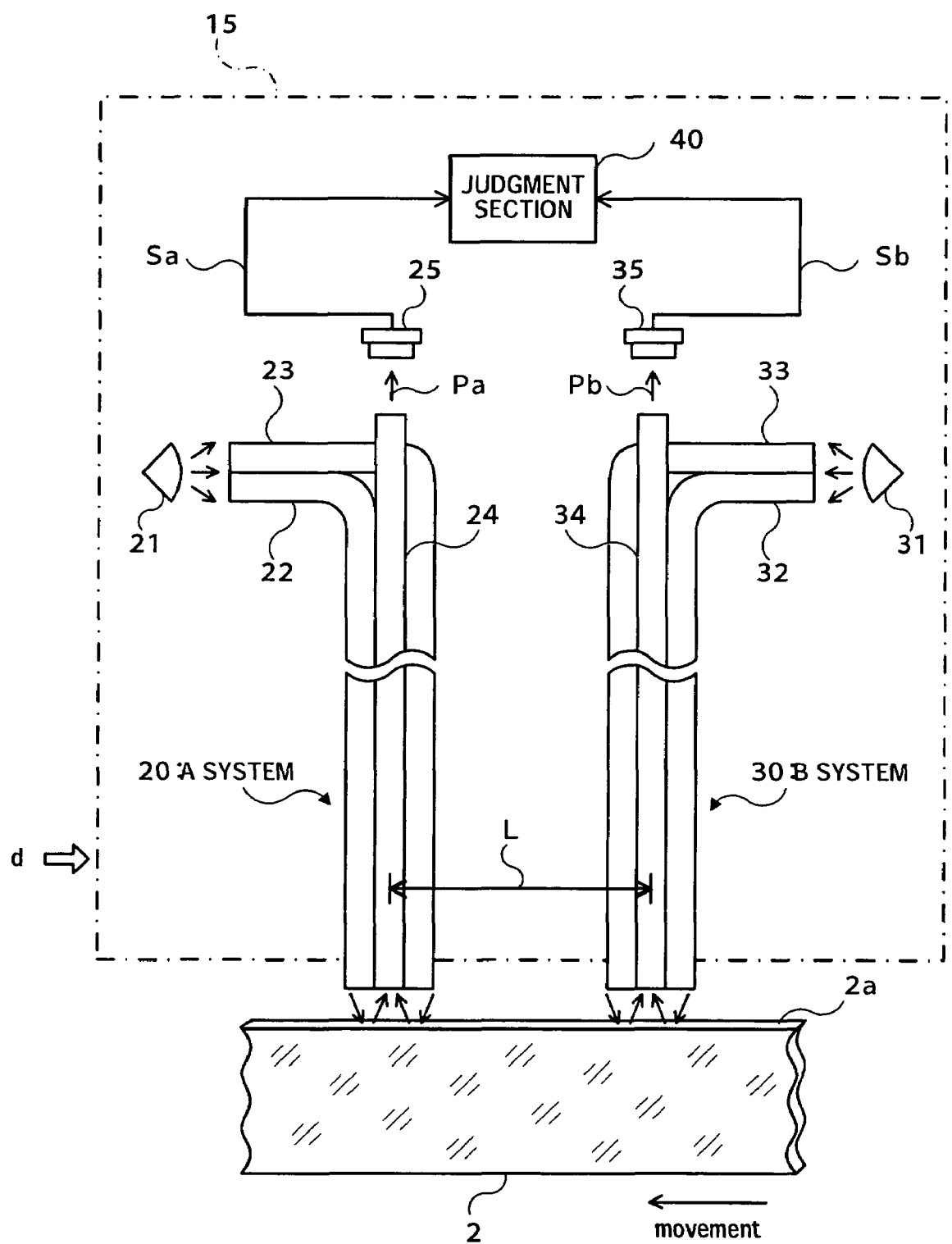
FIG. 2 is a conceptual line block diagram of a defect inspection section 15.

FIG. 2 is a conceptual line block diagram of the defect inspection section 15. Referring to this drawing, the defect inspection section 15 comprises at least two optical sensor sections 20 and 30 (hereinafter denoted as "A system optical inspection section 20" and "B system optical inspection section 30", or simply "A system 20" and "B system 30") and a judgment section 40. The reason for comprising "at least two" the optical sensor sections 20 and 30 is described later.

The A system 20 and B system 30 have the same configuration. Namely, the A system 20 (the B system 30) configuration includes two illuminating optical fibers 22 and 23 (32 and 33) for the purpose of guiding the light from a light source 21 (31) in parallel to an inspectable surface (end face 2a of the metal rings 2) of an object to be inspected (metal rings 2); one light reception optical fiber 24 (34) inserted between the illuminating optical fibers 22 and 23 (32 and 33); and light detectors 25 (35) which convert reflected light Pa (Pb) (light reception intensity) into an electrical signal Sa (Sb) from an inspectable surface guided with the light reception optical fiber 24 (34). The light reception optical fiber 24 constitutes "a first light guiding path" mentioned earlier in the summary of the present invention and a light detector 25 which constitutes "a first light detector" also mentioned in the above summary. Additionally, the light reception optical fiber 34 constitutes "a second light guiding path" and a light detector 35 constitutes "a second light detector" both mentioned in the summary of the present invention.

The judgment section 40 judges whether or not a flaw exists on an inspectable surface of the metal rings 2a based on the electrical signal Sa outputted from the light detector 25 of A system 20 and the electrical signal Sb outputted from the light detector 35 of the B system 30. The basic principle pertains to "the intensity of the light which enters into the two light detectors 25 (35) composed of substantially the same intensity when an inspectable surface does not contain a defect and differs when there is a defect." Also, "the difference value of the electrical signals Sa and Sb outputted from the two light detectors 25 (35) is acquired. When this difference value is greater, this is indicative that an inspectable surface contains a defect and will be discriminated."

In other words, when an inspectable surface of the metal rings 2 does not have a defect, the inspectable surface is a smooth surface and the light from the illuminating optical fibers 22 and 23 (32 and 33) is equally reflected in terms of being smooth and diffused reflection is hardly generated. Accordingly, the intensity of the light which enters into the light detectors 25 (35) is composed of the appropriate strength and substantially the same amount. In this case, the difference value of the electrical signals Sa and Sb are practically set to "0" (zero).

On the other hand when an inspectable surface of the metal rings 2 has a defect, the light from the illuminating optical fibers 22 and 23 (32 and 33) will reflect diffusely at the defective spot. Thus, the intensity of the light guided to the light detectors 25 (35) via the light reception optical fibers 24 (34) only decreases by the amount of diffused reflection. In this case, the spacing of the A system 20 and the B system 30 is separated only by distance L. If this distance L is suitably greater than the above-stated defect size, when the illuminating optical fiber of one system (for example, the light reception optical fiber 24 of the A system 20) guides light declined in strength by the influence of a defect, the light reception optical fiber (light reception optical fiber 34 of the B system 30) of the system on the other side will guide light not declined in strength (namely, intense reflected light strength from a smooth surface without a defect). Consequently, in this case, because the electrical signal Sa becomes less than (<) the electrical signal Sb, the difference value clearly becomes greater as compared with the above-mentioned normal condition (Sa=Sb).

The above principle can be applied as in "when the electrical signals Sa and Sb are outputted from the two light detectors 25 (35), the difference in values is calculated and a greater difference indicates an inspectable surface has a defect which can be discriminated".

The reason at least two systems (the A system 20, the B system 30) are required is as follows: based on the above-stated principal explanation, when an inspectable surface does not contain a defect, the electrical signal Sa (or Sb) outputted from either of the systems constitutes a "greater value." Subsequently, when an inspectable surface contains a defect, while either system is receiving reflected light (declined light strength only by the percentage of diffused reflection) from a defect, the electrical signal Sa (or Sb) outputted from that system constitutes a "lesser value."

In the above principle, a judgment is possible by recognizing these "greater values" and "lesser values." However, from a practicality point of view, this is troublesome and consistent determination of these values cannot be expected. This is because the entire surface including the end faces of the metal rings 2 used in a CVT belt and especially as an object to be inspected becomes lusterless (dull surface finish) inmost cases as a result of nitriding treatment. Furthermore, as the degree of delustering is not standard for each product (or lot) variations occur in the "greater value" of the electrical signal Sa (or Sb) which serves as the standard for normal judging. The optical sensors section is configured with "at least two systems" and when the "difference value" of the electrical signal Sa (or Sb) outputted from these systems is calculated, the influence of the above-stated variations will be eliminated. Thus, consistent judgments can be realized and put into practical use.

Figure 3:
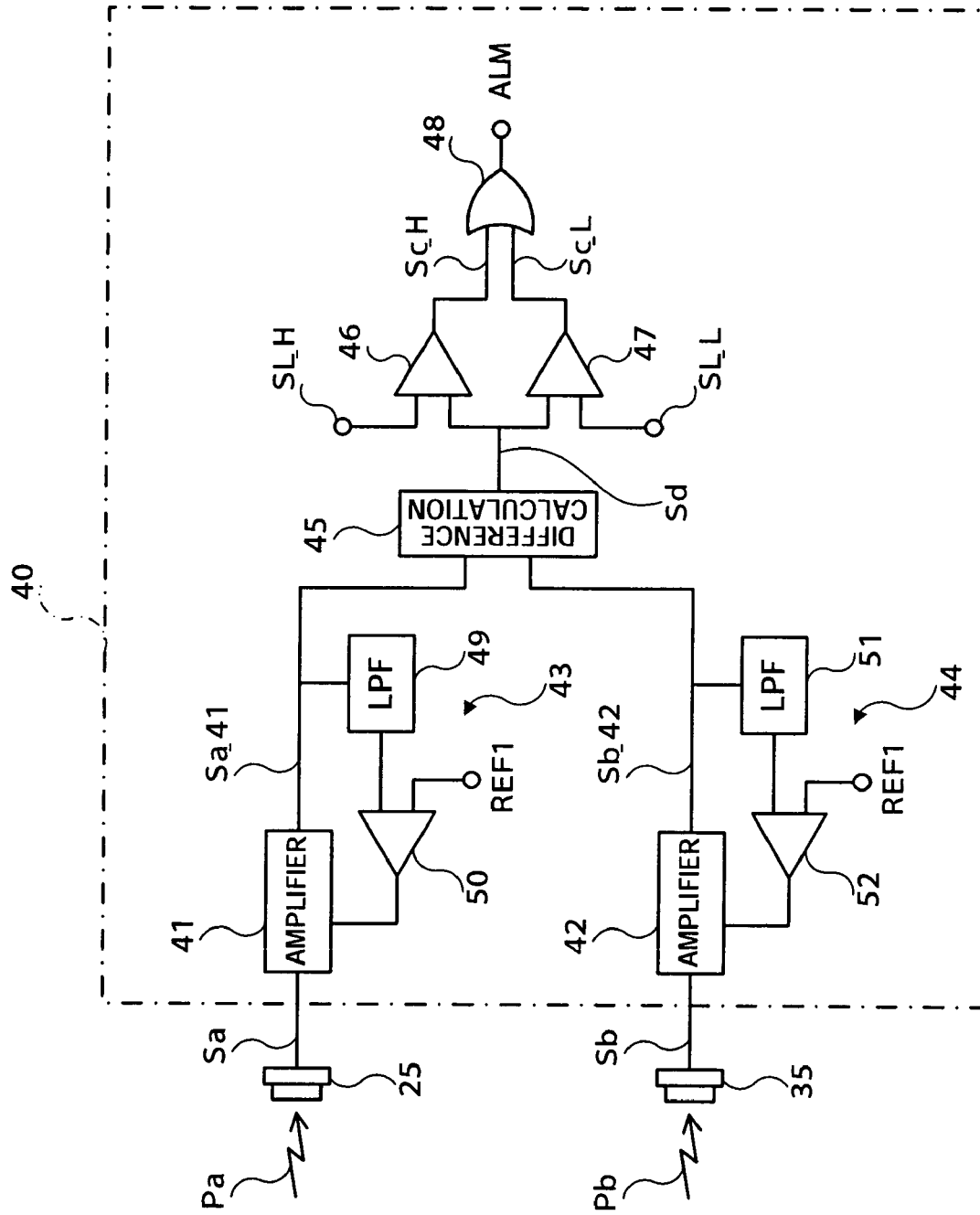
FIG. 3 is a block diagram of a judgment section 40.

FIG. 3 is a block diagram of a judgment section 40. Referring now to this drawing, the judgment section 40 configuration includes an amplifier 41 for A system, an amplifier 42 for the B system, an AGC circuit 43 for A system, an AGC circuit 44 for the B system, a difference calculation section 45 (difference value calculation means), a high side threshold value judgment section 46 (discrimination means), a low side threshold value judgment section 47 (discrimination means) and an alarm signal generation section 48.

The amplifier 41 for the A system amplifies the electrical signal Sa which is outputted from the light detector 25 of the A system and fluctuation control of the amplification factor is performed by the output of the AGC circuit 43 for the A system. The AGC circuit 43 for the A system includes a low-pass filter 49 which extracts only a low-frequency component contained in the continuous current from among the output signals of the amplifier 41 for the A system and a differential amplifier 50 which generates the AGC voltage of the amount corresponding to the difference between the output of the low-pass filter 49 and a predetermined reference voltage REF1. The amplifier 41 for A system amplifies the electric signal Sa by the amplification factor corresponding to this AGC voltage. The purpose of this AGC voltage is to remove low-frequency component "fluctuations" (generated in connection with "surface blurring" of the metal rings 2) contained in the electrical signal Sa.

The amplifier 42 of the B system like the above-stated amplifier 41 for the A system amplifies the electrical signal Sb outputted from the light detector 35 for the B system and fluctuation control of the amplification factor is performed by the output of the AGC circuit 44 for the B system. The AGC circuit 44 for the B system includes a low-pass filter 51 which extracts only a low-frequency component contained in a continuous current from among the output signals of the amplifier 42 for the B system and a differential amplifier 52 which generates the AGC voltage of the amount corresponding to the difference between the output of the low-pass filter 51 and a predetermined reference voltage REF1. The amplifier 42 for the B system amplifies the electrical signal Sb by the amplification factor corresponding to this AGC voltage. The purpose of this AGC voltage is the same as that above which is to remove low-frequency component "fluctuations" contained in the electrical signal Sb.

The difference calculation section 45 calculates a difference value Sd between an electrical signal Sa_41 outputted from the amplifier 41 for the A system and an electrical signal Sb_42 outputted from the amplifier 42 for the B system.

The high side threshold value judgment section 46 compares the difference value Sd calculated in the difference calculation section 45 with a predetermined high side threshold value SL_H and outputs a high side determination result signal Sc_H which becomes active when Sd is greater than SL_H (Sd >SL_H). The low side threshold value judgment section 47 compares the same difference value Sd with a predetermined low side threshold value SL_L and outputs a low side determination result signal Sc_L which becomes active when Sd is greater than SL_L (Sd>SL_L). In addition, the alarm signal generation section 48 outputs an alarm signal ALM indicating defect detection on an inspectable surface when either of these two determination result signals (Sc_H, Sc_L) become active.

Here, the main object of the present invention as stated above is to provide a "the defect inspection device for metal ring end faces which enables automated inspection of end face defects in metal rings 2 along with acquiring improved inspection efficiency, superb precision and reproducibility" will be explained.

Surface defects in the metal rings 2 are not only generated on an end face 2a but also on the peripheral surfaces of these rings. The inner and outer peripheral surface widths are far greater than compared with the width of the end face 2a (a plurality of layered thin metal rings of approximately 0.2 mm in thickness). By employing at least two optical sensor sections 20 and 30 separately and directly facing these inner and outer peripheral surfaces at a predefined minimal distance, defect detection of the inner and outer peripheral surfaces is practicable.

However, in the case of the end face 2a, this configuration (at least two optical sensor sections 20 and 30 erected and directly facing the side end face 2a at a predetermined minimal distance) is simply insufficient and a more suitable design is essential.

This is a description of an example end face defect inspection performed by visual observation. In a defect inspection of an end face 2a by visual observation, the end face 2a is directly viewed or magnified with a loupe (magnifying glass), and the factory worker judges the presence of defects when periphery and variant gloss marks are discovered. However, detection of gloss marks is not a simple process. This is mainly due to the width of an end face 2a being very narrow (seen as an extremely thin sheer line only about 0.2 mm). For this reason, factory workers have to discover the subtle gloss differences in all directions by variously changing the visual recognition direction relative to the end face 2a of the metal rings 2. The present of a defect is then judged by that person from the visual recognition result.

The embodiment applies a common practice in such a visual inspection (When performing a visual inspection by changing the angle of the metal rings 2, a gloss mark on an end face 2a is easy to detect.) and achieves the object of the present invention. Namely, "the defect inspection device for metal ring end faces enables automated inspection of end face defects in metal rings 2 along with acquiring improved inspection efficiency, superb precision and reproducibility".

Figure 4A:
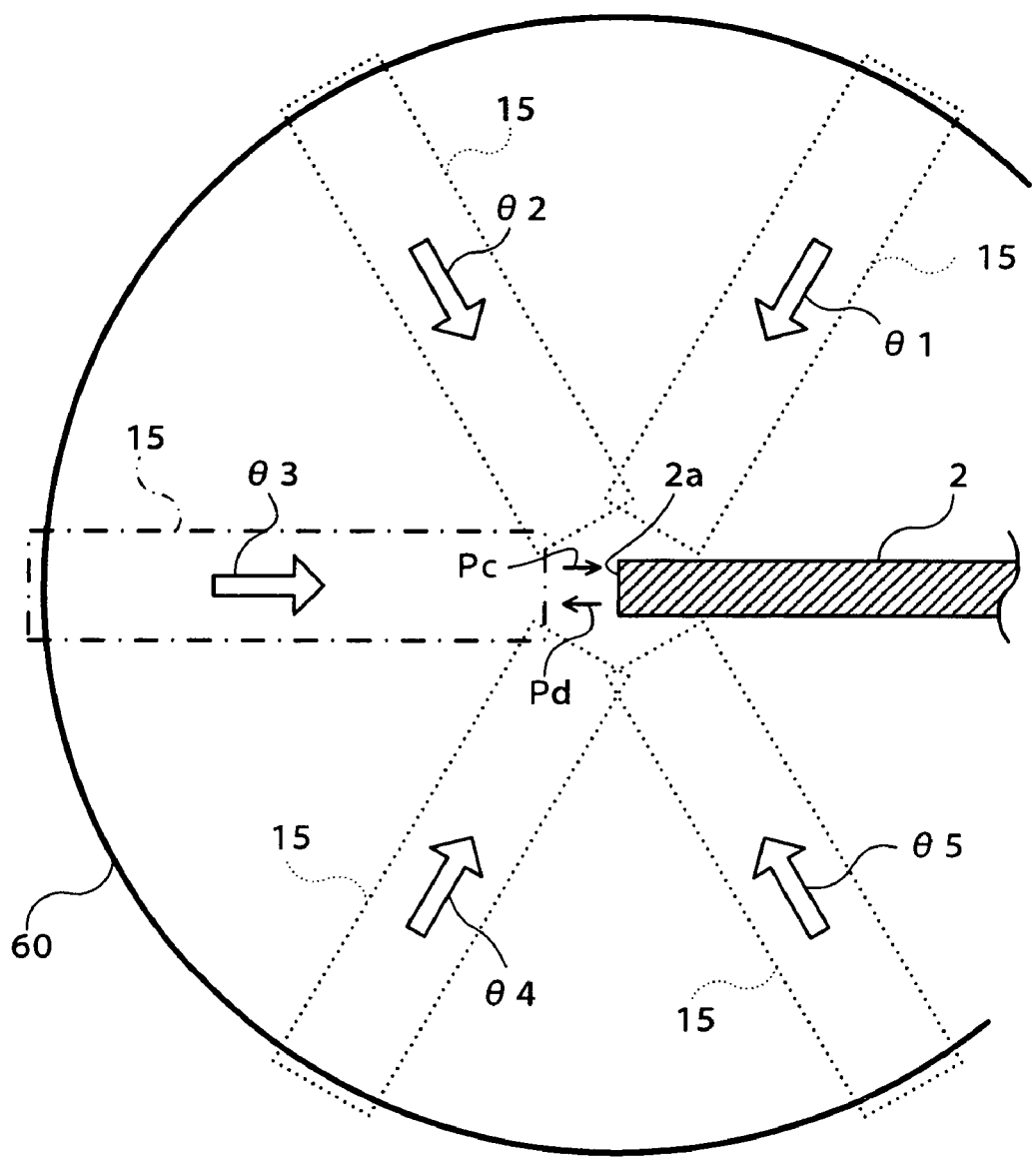
FIGS. 4A and 4B are spatial relationship diagrams of the defect inspection section 15 and the metal rings 2.
Figure 4B:
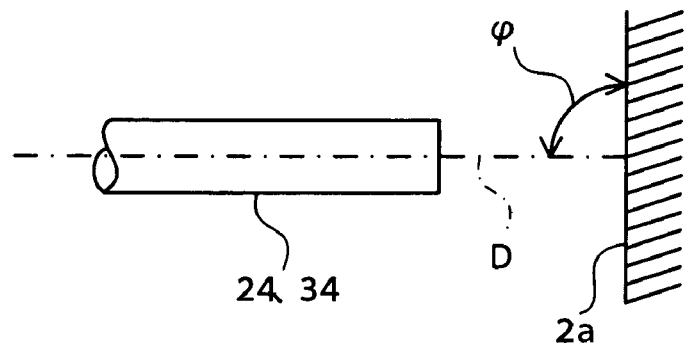

FIGS. 4A and 4B are spatial relationship diagrams of the defect inspection section 15 and the metal rings 2. Additionally, this diagram (FIG. 4A) is a diagram observed from the direction of the arrow "d" in FIG. 2.

In the defect inspection section 15, by following the circular arc shape of an angle modification means 60 reciprocation (alternating backwards and forwards motion) becomes feasible. An inspection light Pc (the illuminating optical fibers 22 and 23 (32 and 33) in FIG. 2) is irradiated from the defect inspection section 15 strikes (shines upon) at various "angles" relative to the end face 2a of the metal rings 2 and follows the movement of the defect inspection section 15. This angle corresponds to "the angle relative to an inspectable surface of the first light guiding path and the second light guiding path" mentioned in the above summary of the invention.

For example, the angles θ1~θ5 in FIG. 4A indicate the representation angle for each inspection light Pc in several movement zones of the defect inspection section 15. As shown in FIG. 4B, these angles θ1~θ5 are also angle θ of the optical axis centerline D of the light reception optical fiber 24 (first light guiding path) and the light reception optical fiber 34 (second light guiding path) in addition to the end face 2a (inspectable surface) of the metal rings 2.

Here, assuming the angle θ3 as a reference angle which constitutes a vertical direction relative to the end face 2a, the angle θ2 is a quantifiable amount greater in a clockwise direction than the reference angle θ3 as well as the angle θ1 is a quantifiable amount further greater in a clockwise direction than the angle θ2. Moreover, the angle θ4 is a quantifiable amount greater in a counter-clockwise direction than the reference angle θ3 as well as the angle θ5 is a quantifiable amount further greater in a counter-clockwise direction than the angle θ4.

Thus, by furnishing the defect inspection section 15 with the circular arc shape of the angle modification means 60 which thereby makes reciprocation possible and by modifying (changing) continuously the inspection light Pc from that defect inspection section 15 between the angles θ1~θ5, the common practice in the above-mentioned visual inspection is adaptable to this configuration. Namely, "when performing a visual inspection by changing the angle of the metal rings 2, a gloss mark on an end face 2a is easy to detect". As a direct result of performing reciprocation of the defect inspection section 15 along the circular arc of the angle modification means 60, automated end face inspections can be achieved while maintaining required efficiency. This is skillfully accomplished by assessing the amount of reflected light Pd from the end face 2a at various angles (θ1~θ5 range) by way of the defect inspection section 15.

Figure 5:
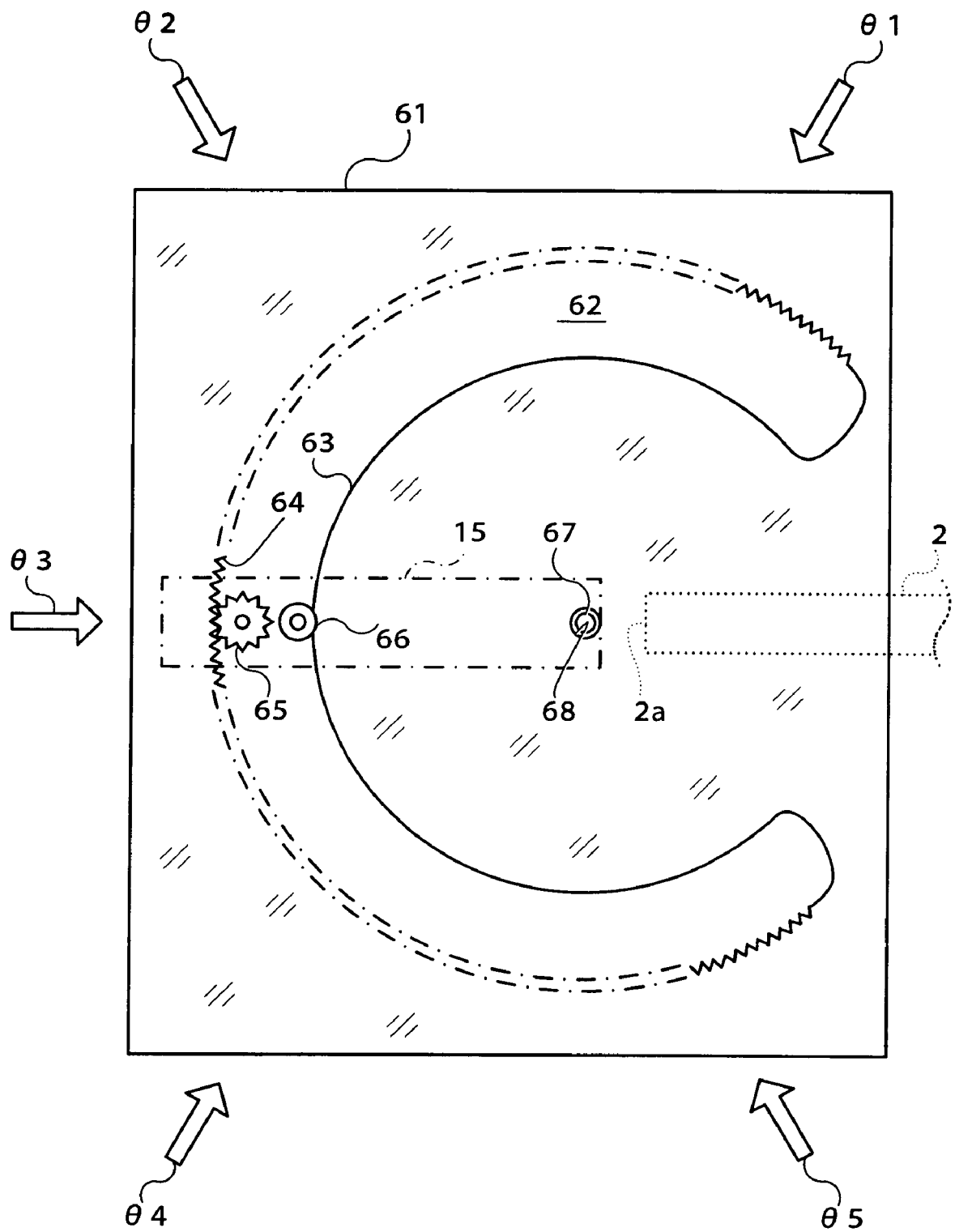
FIG. 5 is a block diagram showing an example of an angle modification means 60.

FIG. 5 is a block diagram showing an example of an angle modification means 60. A plate 61 is bored to form the same curvature of a guide groove 62 circular arc as the above-mentioned angle modification means 60. This guide groove 62 has at least a length which enables displacement of the above-stated angles θ1~θ5. A circular arc surface 63 is formed on the rim (inner rim in the diagram) in one direction of the inner surface of the guide groove 62. A tooth surface 64 is formed on the facing rim (outer side rim in the diagram) which continues over its entirety from end to end. The defect inspection section 15 is provided with a gear 65 which meshes with the tooth surface 64, a roller 66 which freely rolls on the circular arc surface 63 and a pin 67 which serves as the angular displacement (displacement for the angles θ1~θ5) fulcrum (corresponding to a pivot point that is "above the spacing close to the inspectable surface" mentioned in the summary of the invention) of the defect inspection section 15. This pin 67 is inserted and freely rotates in a hole 68 formed in the plate 61. Here, the guide groove 62 circular arc is a portion of a circle which centrally traces an arc based on a supporting point (i.e., the pin 67) above the spacing close to an end face 2a (inspectable surface) of the metal rings 2.

Figure 6A:
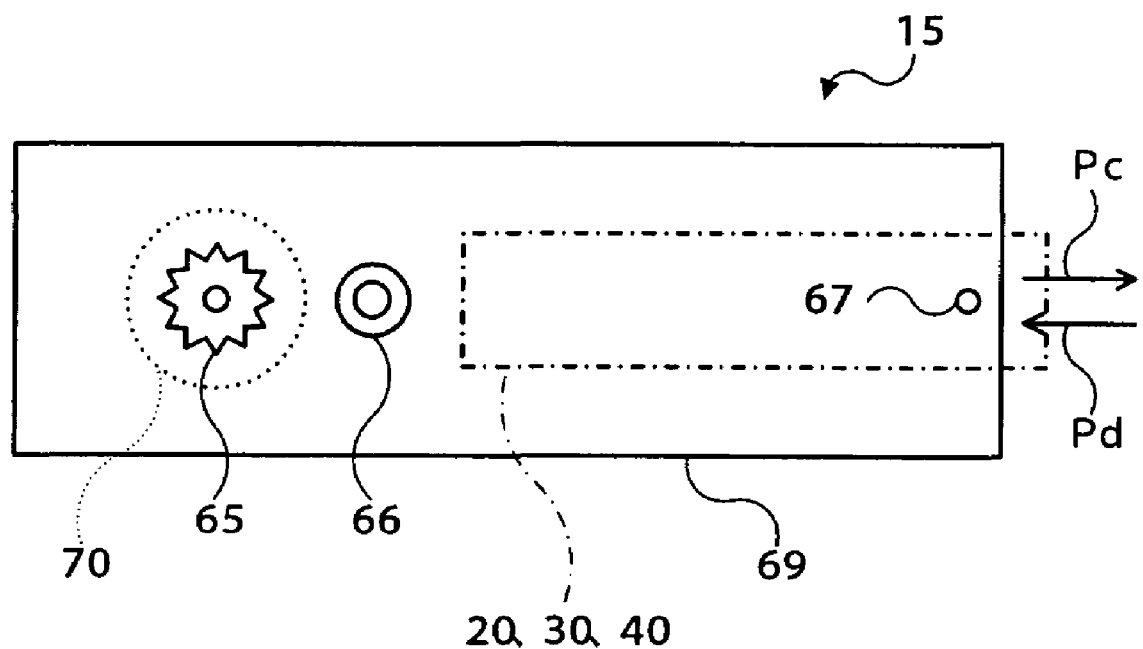
FIGS. 6A and 6B are example outline views of the defect inspection section 15.
Figure 6B:
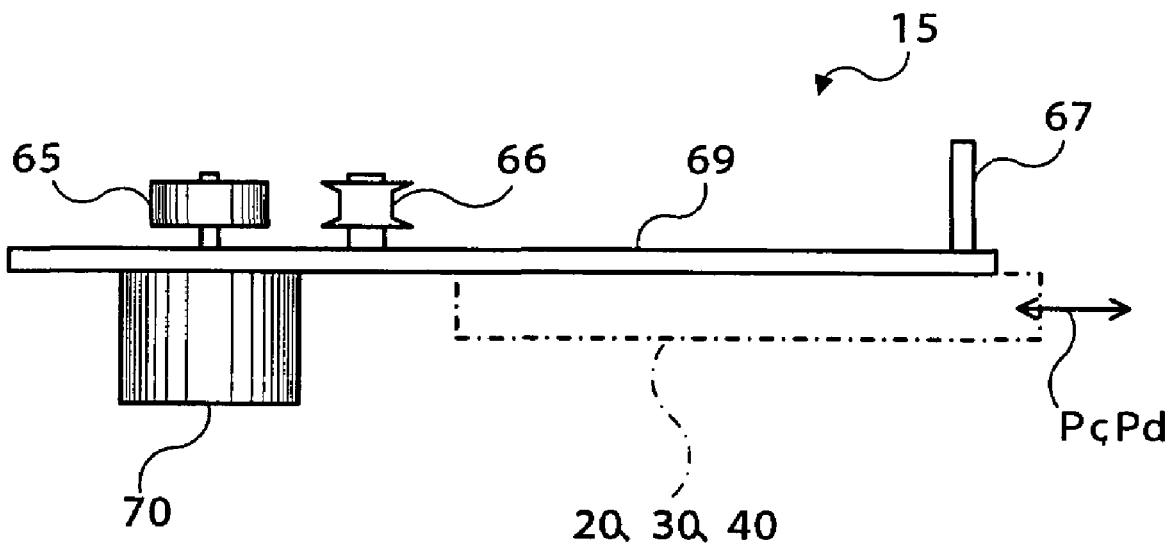

FIGS. 6A and 6B are example outline views of the defect inspection section 15. Referring to the drawing, the defect inspection section 15 has a mounting board 69, a motor 70 for defect inspection angular displacement, the roller 66, the pin 67 and the gear 65 rotated by the motor 70 for defect inspection angular displacement which are installed on the same mounting board 69. Further, the mounting board 69 is mounted with the configuration (optical sensor sections 20 and 30 as well as the judgment section 40) in FIG. 2.

Additionally in outline view of FIG. 6, although the optical sensor sections 20 and 30 together with the judgment section 40 are mounted on the mounting board 69, the present invention is not restricted to this. At least, what is necessary is to mount the light reception optical fibers 24 and 34 (first and second light guiding paths) for guiding the reflected light from the end face 2a (inspectable surface) of the metal rings 2 to the light detectors 25 and 35.

In the above configuration when the motor 70 for angular displacement in the defect inspection section 15 is driven, the gear 65 rotates. This gear 65 moves along according to the guide groove 62, which follows this guided movement and the left end side (the side to which the gear 65 is mounted) of the defect inspection section 15 travels along the guide groove 62. At this stage, because the right end side of the defect inspection section 15 is supported by the plate 61 with the freely rotating pin 67, eventually the defect inspection section 15 is freely displaced in a range of angles θ1~θ5 on the circumference of the fulcrum (pin 67 supporting point) corresponding to the rotation of the motor 70 for angular displacement in the defect inspection section 15.

Accordingly, the common practice in the above-mentioned visual inspection is adaptable to this configuration. Namely, "when performing a visual inspection by changing the angle of the metal rings 2, a gloss mark on an end face 2a is easy to detect".

Figure 7A:
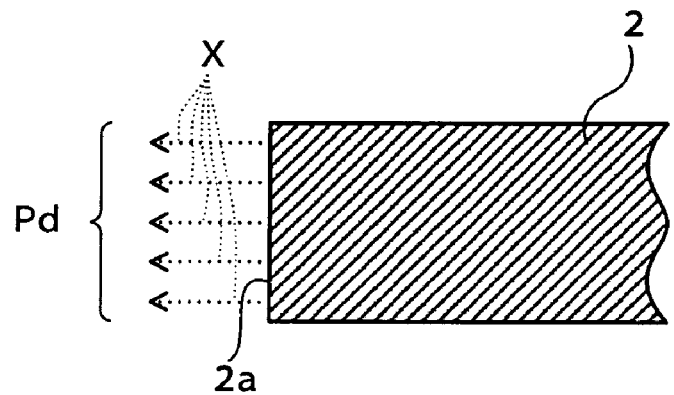
FIGS. 7A~7C are diagrams showing the corresponding relationship between the rotation angles ($\theta1~\theta5$) of the defect inspection section 15 and reflected light Pd from the end face 2a of the metal rings 2.
Figure 7B:
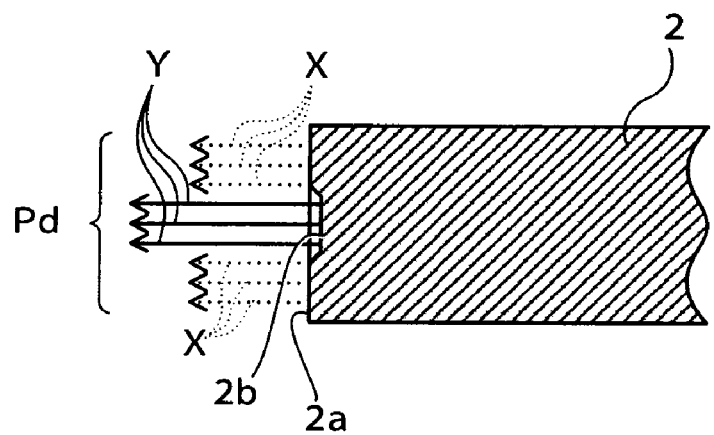
Figure 7C:
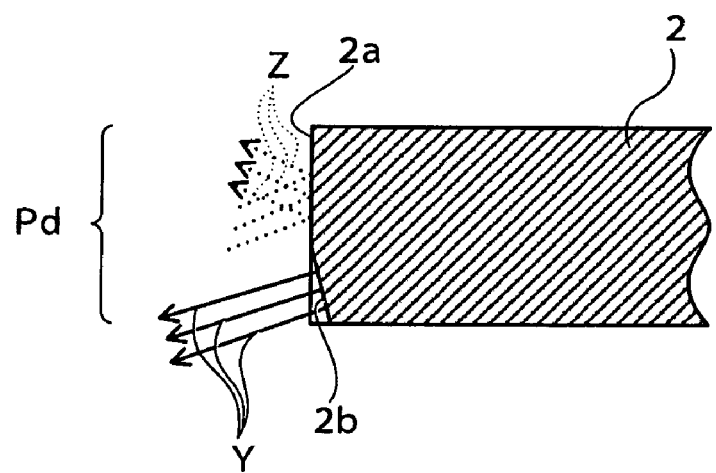
Figure 8A:
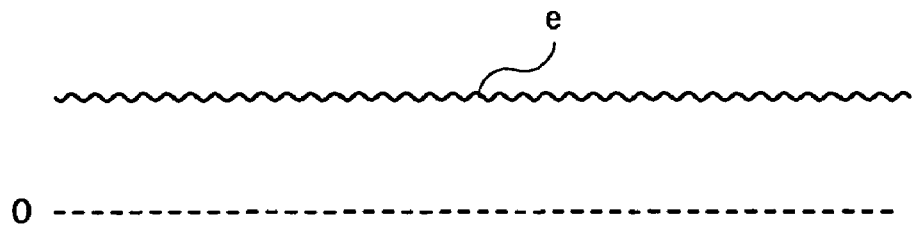
FIGS. 8A~8D are defect detection conceptual diagrams (in the case of no defects) in the defect inspection section 15 of the embodiment.
Figure 8B:
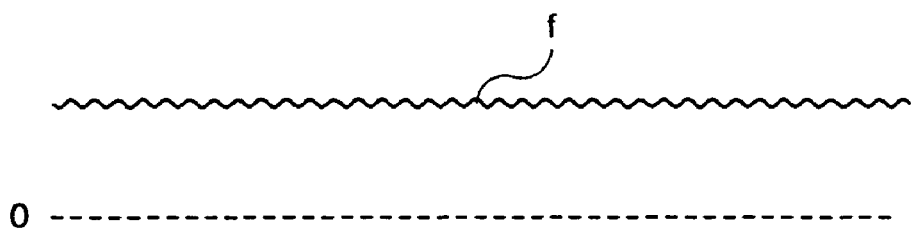
Figure 8C:
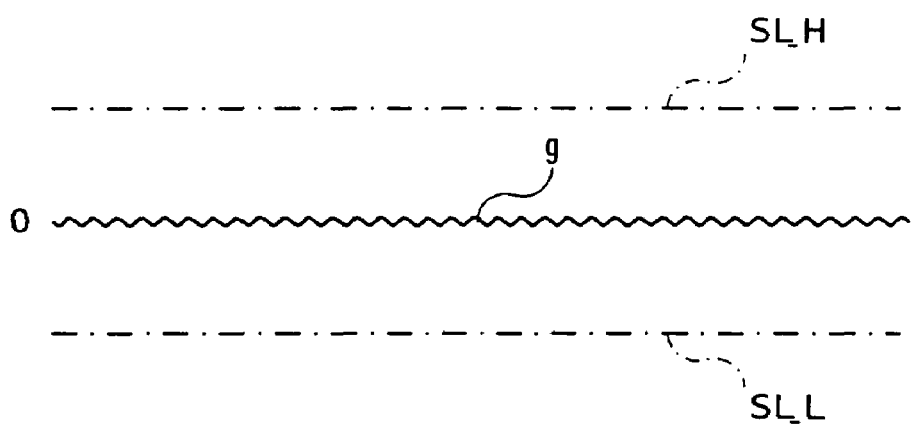
Figure 8D:
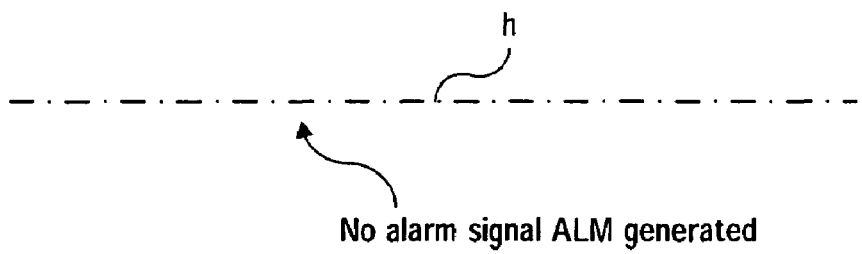
Figure 9A:
FIGS. 9A~9D are defect detection conceptual diagrams (in the case of existing defects) in the defect inspection section 15 of the embodiment.
Figure 9B:
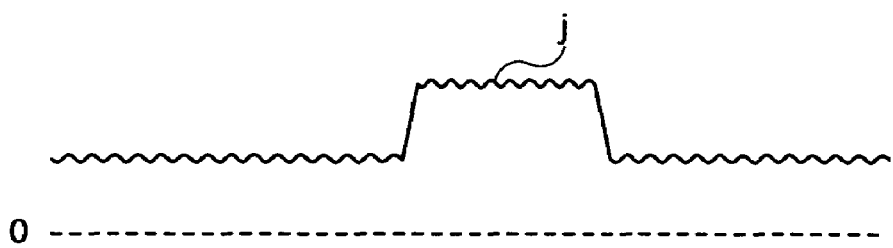
Figure 9C:
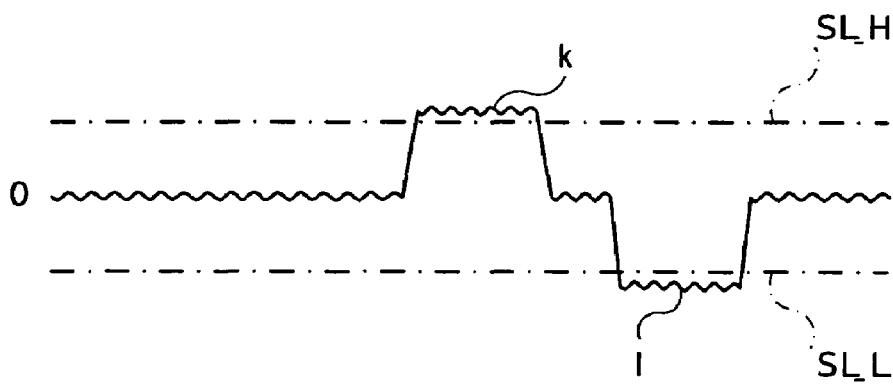
Figure 9D:
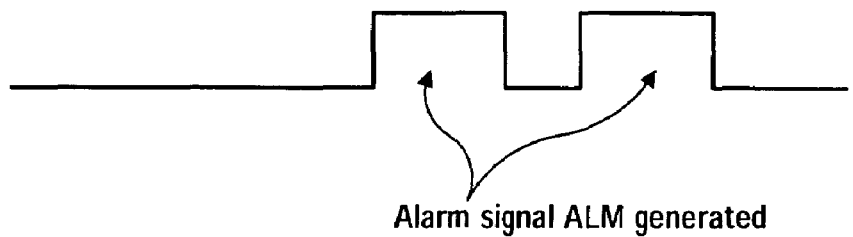
Figure 10:
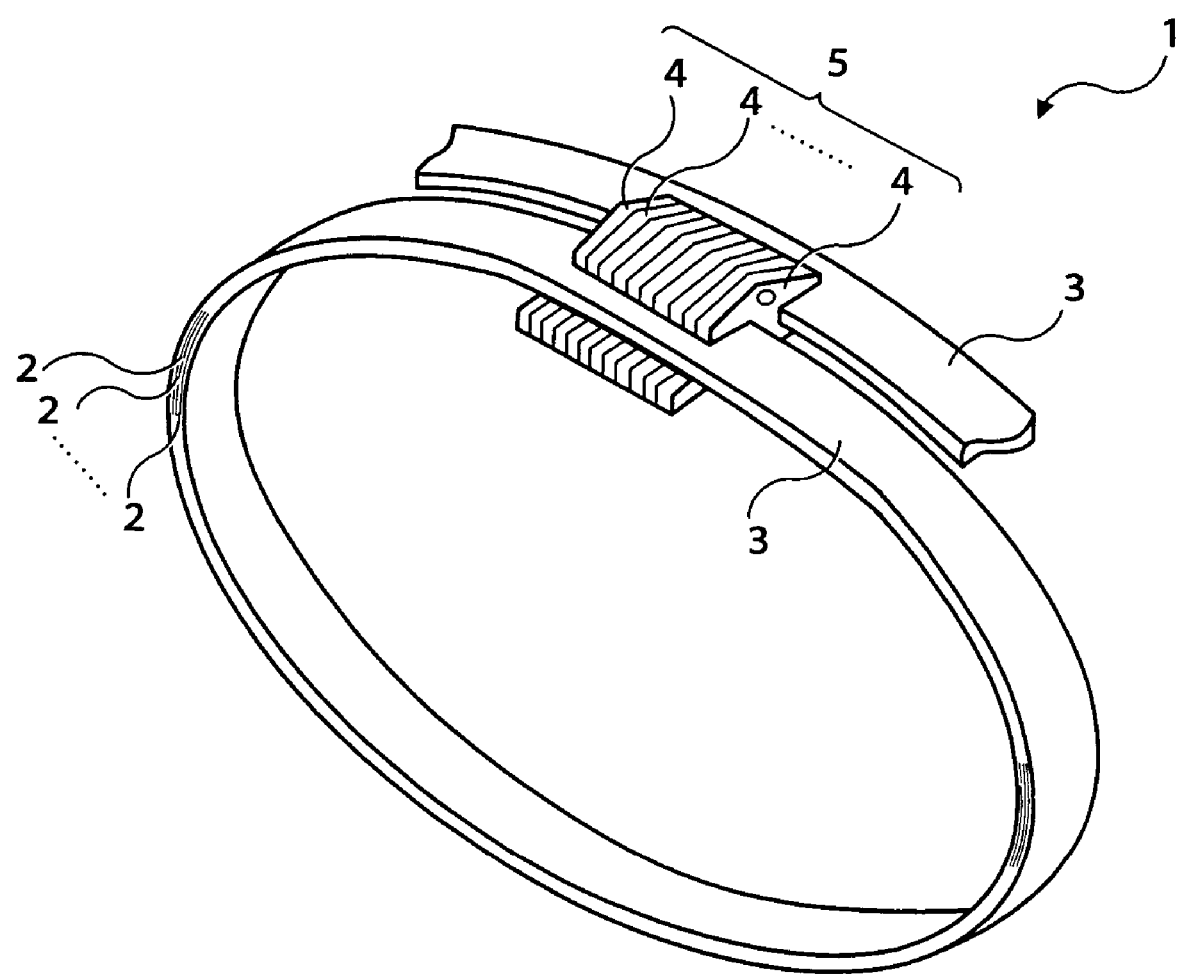
FIG. 10 is an outline view of a CVT belt.
Figure 11:
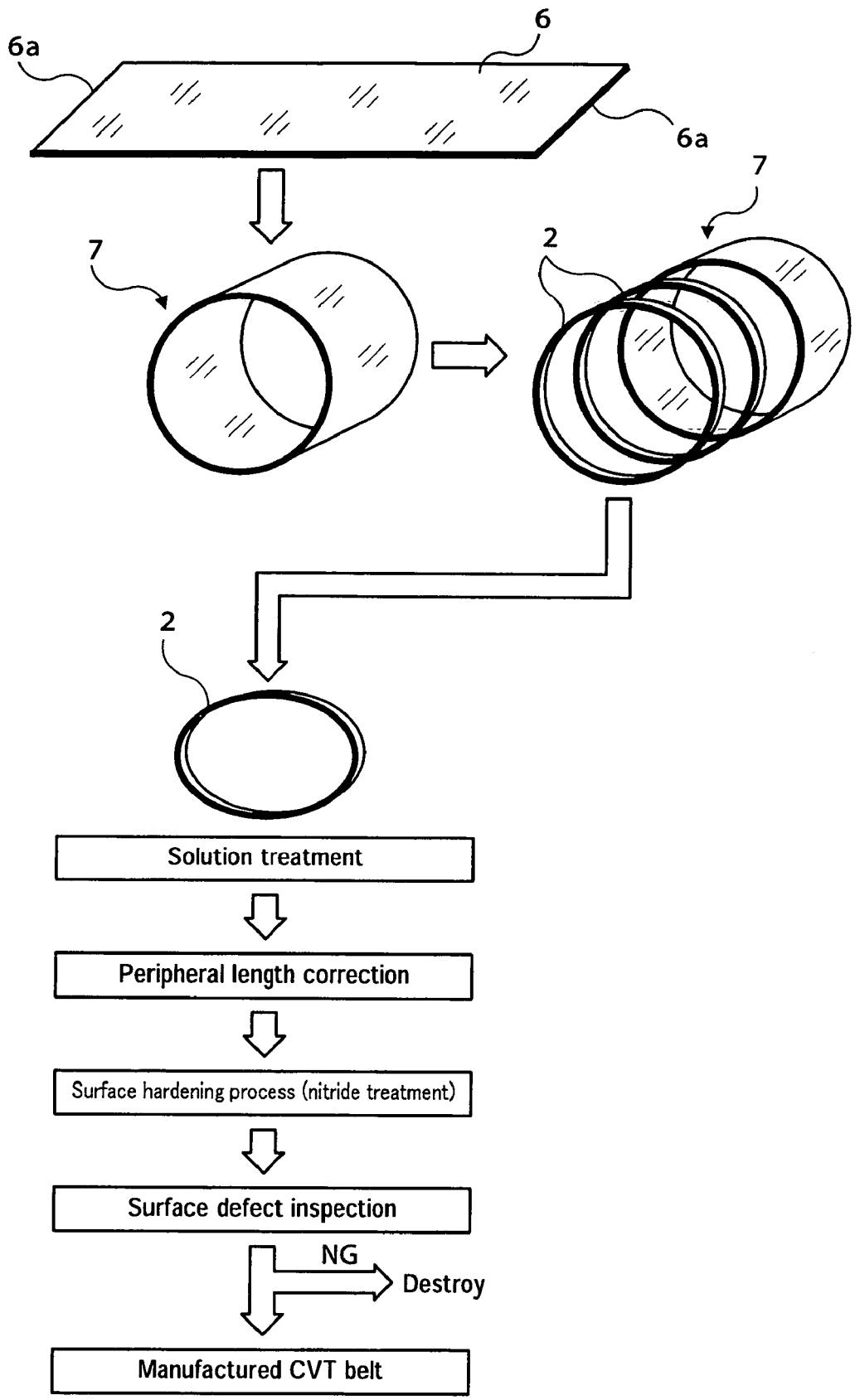
FIG. 11 is an outline diagram of the manufacturing process of the CVT belt 1.
Figure 12A:
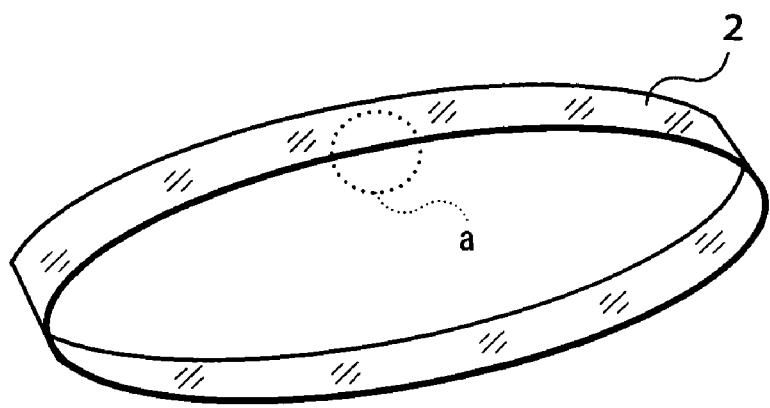
FIG. 12 is a diagram showing an end face defect in one of the metal rings 2.
Figure 12B:
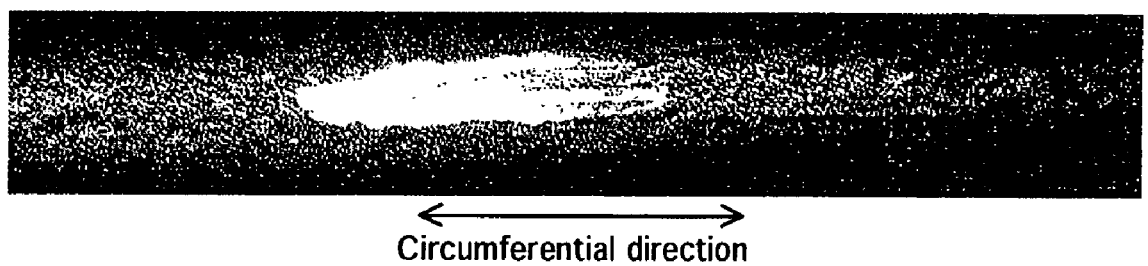
Figure 12C:
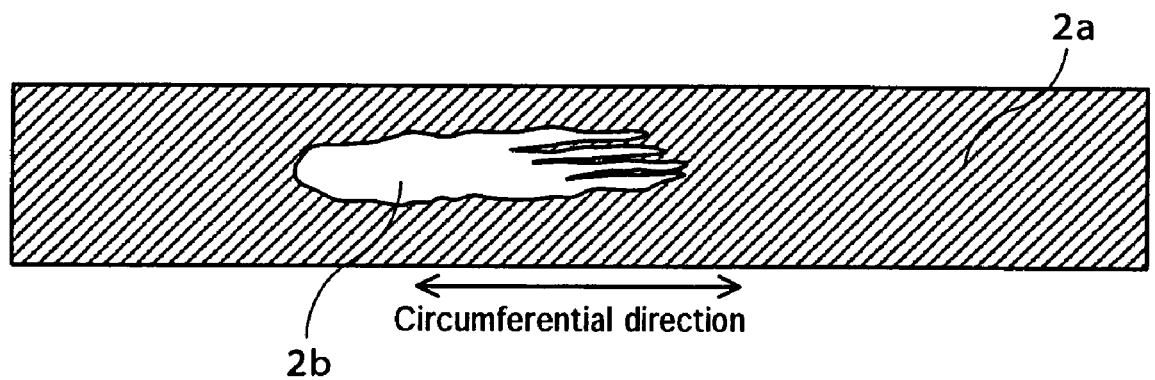

FIGS. 7A~7C are diagrams showing the corresponding relationship between the rotation angles (θ1~θ5) of the defect inspection section 15 and reflected light Pd from the end face 2a of the metal rings 2. FIG. 7A shows a diagram when the rotation position of the defect inspection section 15 is at the reference angle θ3. In this case, the reflected light Pd is reflected substantially vertical over the entire end face 2a. At this point, there are zero defects (no imperfections). Notably, the nitrided layer is not missing, but assumes the end face 2 is in a lusterless state. The reflected light Pa and Pb (light reception intensity) of the defect inspection section 15 in this case is set to "X" for convenience.

FIG. 7B shows a diagram when the rotation position of the defect inspection section 15 is similarly at the reference angle θ3. The difference in FIG. 7A is that a portion of the end face 2a contains a defect 2b. Also, in FIG. 7B like FIG. 7A, although the reflected light Pd is reflected substantially vertical over the entire end face 2a, the reflection intensity of the defect 2b portion in relation to the reflection intensity of the non-defective portion becomes "Y" which is more intense than "X". This is due to the presence of a glossy defect 2b portion and an intense light is reflected.

FIG. 7C shows a diagram when the rotation position of the defect inspection section 15 is at a different position from the reference angle θ3. For example, assuming this is the angle θ4 and contains the defect 2b portion of the end face 2a like the above. This defect 2b is formed diagonally near the corner portion of the end face 2a. Here, when the angle θ4 is substantially in a vertical direction to the defect 2b surface, the reflected light Pd in this case shows the reflection intensity of the defect 2b portion becomes Y is stronger than Z in contrast to the reflection intensity Z (Z<X) of a weaker non-defective portion. This like FIG. 7B is due to the presence of a glossy defect 2b portion and intense light is reflected. Also, the reason Z<X is that a large portion of reflected light does not return to the defect inspection section 15 by the law of reflection (incident angle=reflection angle=θ4).

FIGS. 8A~8D and 9A~9D are defect detection conceptual diagrams in the defect inspection section 15 of the embodiment. In FIG. 8, when the end face 2a of the metal rings 2 does not have a defect (refer to FIG. 7A), the reflected light Pa of the A system and the reflected light Pb of the B system become values (refer to letter "e" in FIG. 8A and "f" in FIG. 8B) in which both exceed "0" (zero) corresponding to X of FIG. 7A. In this case, because the signal levels are substantially equal, both the difference values Sd become practically "0" (zero) (refer to letter "g" in FIG. 8C). Accordingly, because the difference values Sd do not to exceed the threshold values SL_H and SL_L, the alarm signal ALM is not generated (refer to letter "h" in FIG. 8D).

Conversely, as shown in FIG. 9, when the end face 2a of the metal rings 2 has a defect (refer to FIG. 7B and FIG. 7C), a difference corresponding to X and Y in FIG. 7B or Z and Y in FIG. 7C is generated (refer to letter "i" in FIG. 9A and "j" in FIG. 9B) in the reflected light Pa of the A system 20 and the reflected light Pb of the B system 30 (light reception intensity).

In this instance, since both of the difference values Sd constitute significant values other than "0" (zero) in a defective portion (refer to letter "k" and "l" in FIG. 9C), consequently the difference values Sd exceed the threshold values SL_H and SL_L. In that defective portion, an alarm signal ALM is generated (refer to FIG. 9D).

In the embodiment of the present invention, automated rotational movement of the defect inspection section 15 is performed simultaneously as the defect inspection section 15 also performs detection processing (refer to FIGS. 8 and 9). Specifically, while performing two-way displacement by the defect inspection section 15 in a range of angles θ1 to θ5 on the circumference of the fulcrum (pin 67 supporting point) corresponding to the rotation of the motor 70 for angular displacement in the defect inspection section 15, during this period the above-stated detection processing (refer to FIGS. 8 and 9) is accomplished concurrently. Therefore, an automated inspection method is established by adapting the common practice in end face inspections by conventional visual observation, namely, "when performing a visual inspection by changing the angle of the metal rings 2, a gloss mark on an end face 2a is easy to detect", and likewise acquire improved inspection efficiency, superb precision and reproducibility.

Also, although the present invention is designed to perform reciprocation of the defect inspection section 15 in a predetermined range of angles θ1~θ5 on the circumference of the pin 67 supporting point corresponding to the rotation of the motor 70 for angular displacement in the defect inspection section 15, this is only one working example of its operation and does not exclude another equivalent structure. Accordingly, light is irradiated from various directions to the end face 2a of the metal rings 2 and further the configuration enables reflected light from the end face 2a to be received for each of these orientations and a defect inspection can be performed. If another configuration includes these features, an improved design is acceptable.

In the above-described embodiment, although the angle of the "irradiation light" relative to the end face 2a of the metal rings 2 is also changed according to the positional movement (movement of the angles θ1~θ5) of the defect inspection section 15, the present invention is not restricted to this method. What is necessary, at least, is to be able to take in the reflected light from the end face 2a of the metal rings 2 into the defect inspection section 15 continuously in the range of angles θ1~θ5. For example, setting the angle of the irradiation light for the end face 2a of the metal rings 2 as a fixed value (such as the above-described reference angle θ3).

While the present invention has been described with reference to the preferred embodiments, it is intended that the invention be not limited by any of the details of the description therein but includes all the embodiments which fall within the scope of the appended claims.

What is claimed is:

1. A defect inspection device for metal ring end faces of a Continuously Variable Transmission (CVT) V-belt comprising:
   at least two belt pulleys;
   a rotary driving means for rotating said pulleys and a metal ring as an object to be inspected wound around said belt pulleys and for providing circumferential movement to said metal ring;
   a tension assignment means for providing a predetermined tension to said metal ring while regulating the spacing of said belt pulleys during rotation;
   a defect inspection section for inspecting a side end face defect on an inspectable surface of said metal ring during circumferential movement;
   said defect inspection section includes:
   a light source for illuminating said inspectable surface of an object to be inspected;
   a first light guiding path for guiding a reflected light from said inspectable surface to a first light detector and a second light guiding path for guiding said reflected light to a second light detector;
   a difference value calculation means for calculating a difference value between an electrical signal outputted from said first light detector or an electrical signal correlated to the electrical signal outputted from said first light detector and an electrical signal outputted from said second light detector or an electrical signal correlated to the electrical signal outputted from said second light detector;
   a discrimination means for discriminating the presence of a defect on said inspectable surface and comparing said difference value with a predetermined threshold value;
   and further comprises:
   an angle modification means for performing an angle modification operation continuously in a predetermined range relative to said inspectable surface of said first light guiding path and said second light guiding path.

2. The defect inspection device for metal ring end faces according to claim 1, wherein said angle modification means performs an angle modification operation continuously in a predetermined range relative to said inspectable surface of said first light guiding path and said second light guiding path along a predetermined circular arc; and
   said predetermined circular arc forms a portion of a circle which centrally traces an arc above the spacing close to said inspectable surface.

3. The defect inspection device for metal ring end faces according to claim 1, wherein said angle modification means includes:
   a plate;
   a guide groove circular arc formed in said plate;
   a mounting board for performing reciprocation along said guide groove;
   said first light guiding path and said second light guiding path at least are mounted on said mounting board; and
   said guide groove circular arc forms a portion of a circle which centrally traces an arc based on a supporting point above the spacing close to said inspectable surface.

* * * * *